US00PP28400P3

(12) United States Plant Patent
Bradford et al.

(10) Patent No.: US PP28,400 P3
(45) Date of Patent: Sep. 19, 2017

(54) PLUM TREE NAMED 'PLUMRED XII'

(50) Latin Name: *Prunus salicina*
Varietal Denomination: Plumred XII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 34 days.

(21) Appl. No.: 14/757,267

(22) Filed: Dec. 11, 2015

(65) Prior Publication Data

US 2017/0172028 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP19,527 P2 12/2008 Bradford
PP23,719 P3 7/2013 Bradford

*Primary Examiner* — Keith Robinson

(57) ABSTRACT

The present invention relates to a plum tree and more particularly to a new and distinct variety broadly characterized by a medium to large size, vigorous, hardy, and productive tree. Being self-unfruitful, the present variety requires cross pollination from an apricot, interspecific, or plum that blooms during the mid to late season, such as 'September Yummy' plum (U.S. Plant Pat. No. 14,220). The present variety produces a medium amount of bloom with plenty of pollen to entice good bee activity to facilitate pollination. The fruit matures under the ecological conditions described during the last part of September, with first picking on Sep. 21, 2015, and will hang on the tree an additional twenty days. The fruit is uniformly medium to large in size, full red in skin color, full red in flesh color, semi-freestone in type, mostly oblate in shape, firm in texture, very sweet, and excellent in flavor.

1 Drawing Sheet

Botanical classification: *Prunus salicina.*
Varietal denomination: 'PLUMRED XII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumred XII'.

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'Black Majesty' plum tree (U.S. Plant Pat. No. 19,527) was crossed by us in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H21". They were grown as seedlings on their own root in our greenhouse and upon reaching dormancy transplanted to a cultivated area of our experimental orchard located near Le Grand, Calif. in Merced County (San Joaquin Valley). During the summer of 2011 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Black Majesty' plum (U.S. Plant Pat. No. 19,527), by having a medium size tree, by blooming in the medium to late season, by being self-unfruitful and by producing fruit that is firm, juicy, and very sweet, but is distinguished therefrom by producing fruit that is somewhat larger in size, that is semi-freestone instead of clingstone in type, that is red instead of black in skin color, that is full red instead of yellow in flesh color, and that matures about thirty days later.

The present variety is most similar to 'Plumred IX' interspecific tree (U.S. Plant Pat. No. 23,719), by having a medium to large size tree, by being self-unfruitful, by blooming in the mid to late season, and by producing fruit that is nearly full red in skin color, mostly red in flesh color, and very sweet, but is distinguished therefrom by producing fruit that is semi-freestone instead of clingstone in type, that is much larger in size, and that matures about thirty days later.

SUMMARY OF VARIETY

The present plum variety is characterized by a medium to large size, vigorous, hardy, and productive tree. Being self-unfruitful, the present variety requires cross pollination from an apricot, interspecific, or plum that blooms during the mid to late season, such as 'September Yummy' plum (U.S. Plant Pat. No. 14,220). The present variety produces a medium amount of bloom with plenty of pollen to entice good bee activity to facilitate pollination. The fruit matures under the ecological conditions described during the last part of September, with first picking on Sep. 21, 2015, and will hang on the tree an additional twenty days. The fruit is uniformly medium to large in size, full red in skin color, full red in flesh color, semi-freestone in type, mostly oblate in shape, firm in texture, very sweet, and excellent in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the full ripe on Oct. 6, 2015, on the original tree during its eighth growing season. The flower and bud descriptions were developed during the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Black Majesty' (U.S. Plant Pat. No. 19,257) plum.

Pollen parent: Unknown.

TREE

Size: Medium to large, reaching a height of 12' [3.66 m.] and a spread of 6' [1.83 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and Dense.

Form: Pruned to a Perpendicular V type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'September Yummy' (U.S. Plant Pat. No. 14,220) plum tree.

Bearing: Regular bearer, weather dependent, with no crop failures observed as of yet.

Trunk:

*Size*.—Medium, reaching a maximum diameter of 4" [102 mm.] after the eighth growing season.

*Texture*.—Medium shaggy.

*Bark color*.—A Grayish brown [61. gy.Br] and Dark brown [59. d.Br] variegation with Moderate orange [53. m.O] crevices present.

*Lenticels*.—Approximate Number Per Square Inch: 8. Color: Strong brown [55. s.Br]. Average Size: ¼" [6.4 mm.] in length. The width is typically one fourth as much as the length. Shape: Eye-shaped.

Branches:

*Size*.—Medium to slender, diameter of the scaffold is 2¼" [57 mm.] measured 12" above the crotch, diameter of secondary limb is 1¼" [32 mm.], diameter of lowest side hanger is 1" [25 mm.] measured 6" from the scaffold.

*Texture*.—Smooth on first and second year wood, increasing in roughness with age.

*Color*.—1st Year Wood Topside: Grayish red [19. gy.R]. 1st Year Wood Underside: Brilliant yellow green [116. brill.YG]. 2nd Year Wood: Grayish brown [61. gy.Br] with Light grayish yellowish brown [79. l.gy.yBr] crevices.

*Lenticels*.—Number Per Square Inch: About 30 on second year wood. Color: Light yellowish brown [76. l.yBr]. Average Size: Small, 1/32" [0.8 mm.] in length. The width is typically one fourth as much as the length. Shape: Eye-shaped.

Leaves:

*Size*.—Medium. Average Length: 4½" [114.3 mm.]. Average Width: 1 3/16" [30.2 mm.].

*Arrangement*.—Alternate.

*Thickness*.—Medium.

*Form*.—Elliptical.

*Apex*.—Acuminate.

*Base*.—Acute with an average angle base angle of 75 degrees.

*Surface*.—Smooth on both sides.

*Color*.—Dorsal Surface: Moderate olive green [125. m.OlG]. Ventral Surface: Deep yellow green [118. deep YG].

*Margin*.—Finely serrate.

*Venation*.—Pinnately net veined.

*Petiole*.—Average Length: ½" [12.7 mm.]. Average Thickness: 1/16" [1.6 mm.]. Color: Moderate yellow green [120. m.YG] with some Grayish reddish orange [39. gy.rO] areas where exposed to sunlight.

*Stipules*.—Number: Usually 2 per leaf, up to 6 per growing tip. Average Length: ¼" [6.4 mm.]. Color: Pale yellow green [121. p.YG] becoming Grayish reddish brown [46. gy.rBr] with age.

*Glands*.—Number: Usually 2 to 4 per leaf. Position: Usually alternate, positioned near the intersection of the petiole and the leaf blade. Form: Globose. Size: Medium, 1/48" [0.5 mm.] in diameter. Color: Brilliant yellow green [116. brill.YG] becoming Grayish reddish brown [46. gy.rBr] with age. Leaf buds: Pointed.

Flower buds:

*Hardiness*.—Hardy, with respect to central California blooming season.

*Diameter*.—Typically 3/16" [4.8 mm.] 1 week before bloom.

*Length*.—Typically 3/8" [9.5 mm.] 1 week before bloom.

*Form*.—Not appressed.

*Surface*.—Slightly pubescent.

*Tip color*.—White [263. White].

Flowers: Perfect, complete, perigynous, usually a single pistil, typically thirty or more stamens, five sepals and petal locations alternately positioned.

*Average flower diameter*.—1" [25.4 mm.].

*Average flower depth*.—3/8" [9.5 mm.] when fully open.

*Average pedicel length*.—3/16" [4.8 mm.].

*Number of petals*.—Five, no double blossoms observed.

*Petal shape*.—Oval to circular.

*Petal margin*.—Entire, slightly wavy.

*Average petal diameter*.—1/2" [12.7 mm.].

*Average petal length*.—9/16" [14.3 mm.].

*Petal apex*.—Rounded.

*Petal base*.—Obtuse.

*Petal color*.—White [263. White] on both sides.

*Anther color*.—Light yellow [86. l.Y].

*Pollen production*.—Moderate, average enticement to bees.

*Stigma color*.—Light greenish yellow [101. l.gY].

*Stigma position*.—Located about even with the surrounding anthers.

*Sepal color*.—Brilliant yellow green [116. brill.YG] on both sides.

*Sepal length*.—7/32" [5.6 mm.].

*Sepal width*.—5/32" [4.0 mm.].

*Sepal apex*.—Rounded to elliptical to match the width and length.

*Sepal margin*.—Fairly smooth, slightly serrated toward the apex.

*Average pistil length*.—9/16" [14.3 mm.].

*Average stamen length*.—1/2" [12.7 mm.].

*Ovary*.—Smooth.

*Fragrance*.—Moderate.

*Pollen production*.—Moderate, average bee enticement.

*Pollen color*.—Strong yellow [84. s.Y].

*Blooming period*.—Medium to late, about three days after 'Santa Rosa' plum (unpatented).

*Onset of bloom*.—One percent on Feb. 21, 2015.

*Date of full bloom*.—Mar. 3, 2015.

*Duration of bloom*.—One to two weeks, dependent on ambient temperature.

*Bloom density*.—Moderate.

*Number per cluster*.—2 to 6, mostly 2.

FRUIT

Maturity when described: Full ripe, Oct. 6, 2015.

Date of first picking: Sep. 21, 2015.

Date of last picking: Oct. 10, 2015.

Size: Uniform, medium to large.

*Average diameter axially*.—2 5/16" [58.7 mm.].

*Average diameter across cheek plane*.—2 11/16" [68.3 mm.].

*Average diameter across suture plane*.—2 5/8" [66.7 mm.].

*Typical weight*.—5.7 ounces [162 grams].

Form: Somewhat variable, mostly oblate with a few cordate, compressed axially.

*Longitudinal section form*.—Mostly oblate.

*Transverse section through diameter*.—Round.

Suture: A shallow groove extending from the base just to the apex, with a slight depression beyond the pistil point.

Ventral surface: Rounded, lipped very slightly on both sides.

Lips: Slightly unequal.

Cavity: Flaring, elongated in suture plane, suture showing on one side.

*Depth*.—5/16" [7.9 mm.].

*Breadth*.—15/16" [23.8 mm.].

*Stem markings*.—Usually not present.

Base: Truncate, somewhat cordate if viewed parallel to the suture.

Apex: Mostly rounded, about twenty percent mammiform.

Pistil point: An inconspicuous Dark grayish yellow [91.d.gy.Y] dot.

Stem: Medium.

*Average length*.—7/16" [11.1 mm.].

*Average width*.—1/8" [3.2 mm.].

Skin:

*Thickness*.—Medium.

*Surface*.—Smooth.

*Tenacity*.—Tenacious to the flesh.

*Astringency*.—Moderate.

*Tendency to crack*.—None observed.

*Color*.—Very deep red [14. v.deep R] over a Deep red [13. deep R] background with Light yellow [86. l.Y] freckling throughout.

*Lenticels*.—Number Per Square Inch: About 60 toward the apex. Average diameter: 1/48" [0.5 mm].

*Bloom*.—Moderate to heavy.

Flesh:

*Color*.—Moderate red [15. m.R] with Light yellowish pink [28. l.yPk] fibers visible throughout.

*Surface of pit cavity*.—Covered with Dark red [16. d.R] fibers.

*Amygdalin*.—Abundant.

*Juice*.—Abundant, rich.

*Texture*.—Firm, crisp, meaty.

*Fibers*.—Abundant, tender.

*Ripens*.—Slightly earlier on the shoulders.

*Flavor*.—A tasty balance of acid and sugar, typically 25 brix.

*Aroma*.—Slight.

*Eating quality*.—Excellent.

STONE

Type: Semi-freestone.

Form: Obovate.

Hilum: Narrow, oval.

Base: Truncate to round.

Apex: Acute.

Sides: Mostly equal.

Surface: Fairly smooth with rounded ridges toward the base.

External color of stone: Light brown [57. l.Br] when first removed.

Pit wall color when cracked: Light orange yellow [70. l.OY].

Cavity surface color: Moderate yellowish brown [77. m.yBr] with a Moderate orange yellow [71. m.OY] middle.

Average pit wall thickness: 1/8" [3.2 mm.].
Average length: 1" [25.4 mm.].
Average width: 3/4" [19.1 mm.].
Average breadth: 5/16" [7.9 mm.].
Tendency to split: None observed.
Kernel:

*Form*.—Oval.
*Skin color*.—Light yellowish brown [76. l.yBr] when first removed.
*Pellicle color*.—Deep yellowish brown [75. deep yBr].
*Vein color*.—Deep yellowish brown [75. deep yBr].
*Taste*.—Bitter.
*Viable*.—Yes.
*Average length*.—9/16" [14.3 mm.].
*Average width*.—3/8" [9.5 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Plumred IX' interspecific tree (U.S. Plant Pat. No. 23,719), by having a medium to large size tree, by being self-unfruitful, by blooming in the mid to late season, and by producing fruit that is nearly full red in skin color, mostly red in flesh color, and very sweet, but is distinguished therefrom by producing fruit that is semi-freestone instead of clingstone in type, that is much larger in size, and that matures about thirty days later.

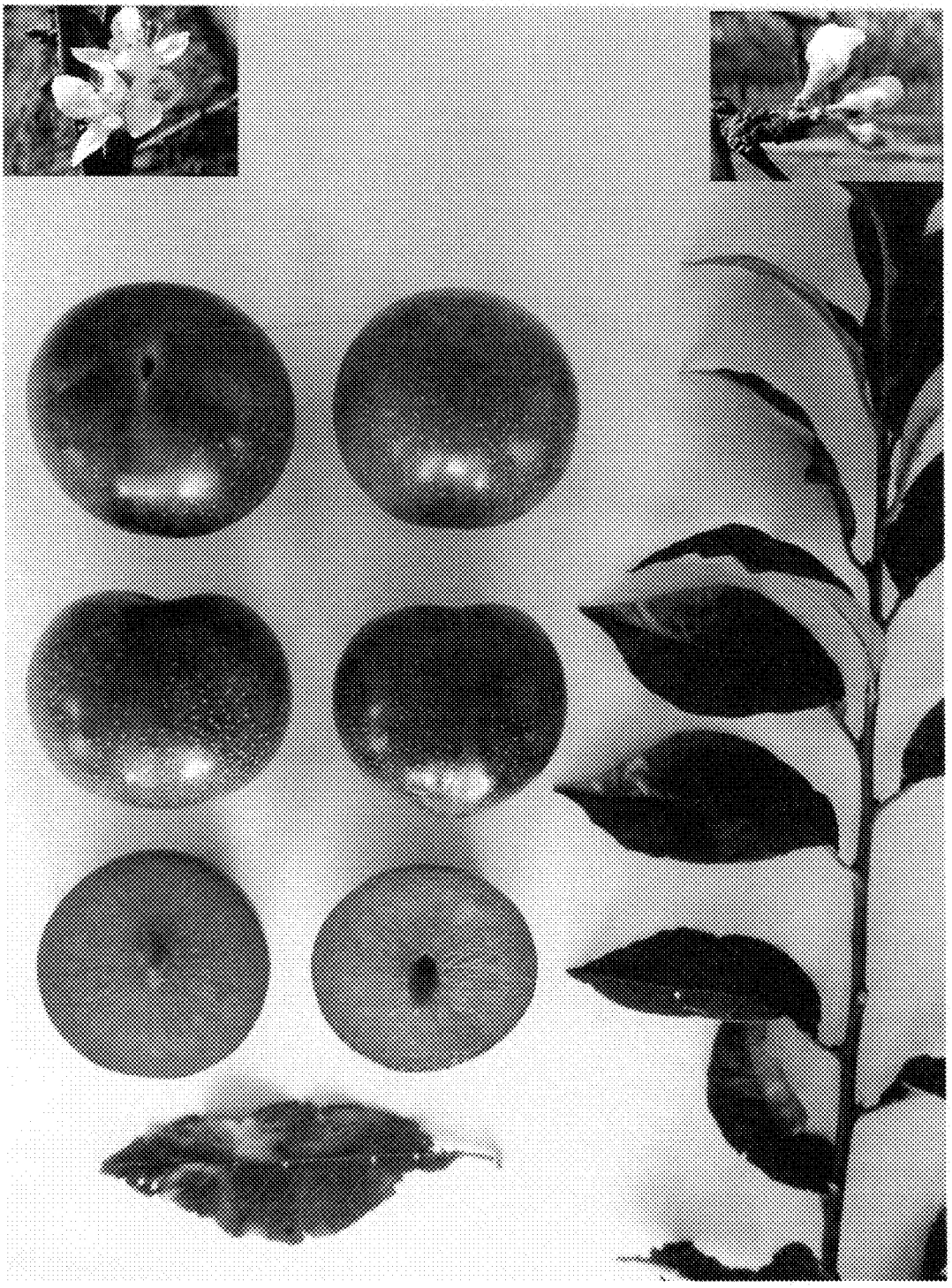

* * * * *